United States Patent
Lenzner et al.

(10) Patent No.: US 7,721,743 B2
(45) Date of Patent: May 25, 2010

(54) DEVICE AND PROCEDURE FOR REFRACTIVE LASER SURGERY

(75) Inventors: Matthias Lenzner, Berlin (DE); Georg Korn, Kleinmachnow (DE); Olaf Kittelmann, Kleinmachnow (DE)

(73) Assignee: Katana Technologies GmbH, Kleinmachnow (DE)

( * ) Notice: Subject to any disclaimer, the term of this patent is extended or adjusted under 35 U.S.C. 154(b) by 1059 days.

(21) Appl. No.: 10/501,567

(22) PCT Filed: Jan. 9, 2003

(86) PCT No.: PCT/EP03/00136

§ 371 (c)(1),
(2), (4) Date: Jul. 12, 2004

(87) PCT Pub. No.: WO03/057100

PCT Pub. Date: Jul. 17, 2003

(65) Prior Publication Data

US 2005/0085800 A1    Apr. 21, 2005

(30) Foreign Application Priority Data

Jan. 10, 2002 (DE) ................. 102 00 763
Feb. 15, 2002 (DE) ................. 102 06 663

(51) Int. Cl.
*A61B 19/00* (2006.01)
*A61B 18/20* (2006.01)

(52) U.S. Cl. ................. 128/898; 606/4; 606/10; 606/17

(58) Field of Classification Search .......... 606/3–6, 606/10, 13, 17, 18; 607/88, 89; 128/898
See application file for complete search history.

(56) References Cited

U.S. PATENT DOCUMENTS

| 3,782,925 | A | | 1/1974 | Brandis et al. ................. 75/124 |
| 5,035,693 | A | * | 7/1991 | Kratzer et al. ................. 606/12 |
| 5,144,630 | A | | 9/1992 | Lin ............................. 372/22 |
| 5,984,916 | A | | 11/1999 | Lai ............................. 606/11 |
| 5,995,867 | A | * | 11/1999 | Zavislan et al. ............... 600/476 |
| 6,210,401 | B1 | * | 4/2001 | Lai ............................. 606/12 |
| 6,373,869 | B1 | * | 4/2002 | Jacob .......................... 372/22 |
| 6,687,035 | B2 | * | 2/2004 | Knebel et al. ................. 359/204 |
| 6,693,931 | B1 | * | 2/2004 | Mendenhall et al. ... 372/29.023 |
| 6,726,680 | B1 | * | 4/2004 | Knopp et al. .................. 606/12 |
| 7,238,176 | B2 | * | 7/2007 | Loesel et al. .................. 606/5 |
| 7,252,662 | B2 | * | 8/2007 | McArdle et al. ............... 606/5 |
| 2002/0054613 | A1 | * | 5/2002 | Kang ........................... 372/22 |

FOREIGN PATENT DOCUMENTS

| EP | 0145471 | 6/1985 |
| EP | 1138291 | 10/2001 |
| EP | 1159986 | 12/2001 |
| FR | 2790485 | 9/2000 |
| JP | 6117251 | 6/1986 |
| JP | 7157852 | 6/1995 |

* cited by examiner

*Primary Examiner*—Ahmed M Farah
(74) *Attorney, Agent, or Firm*—Abelman, Frayne & Schwab

(57) ABSTRACT

The invention involves a device and a procedure for refractive laser surgery on a target object. With the aid of a laser beam source, an fs-impulse laser beam is generated. A second laser beam source generates a UV laser beam. A shared scanner device utilizes the fs-impulse laser beam and the UV laser beam for the scanning of the target object.

5 Claims, 1 Drawing Sheet

DEVICE AND PROCEDURE FOR REFRACTIVE LASER SURGERY

BACKGROUND OF THE INVENTION

1. Field of the Invention

Figure 1:
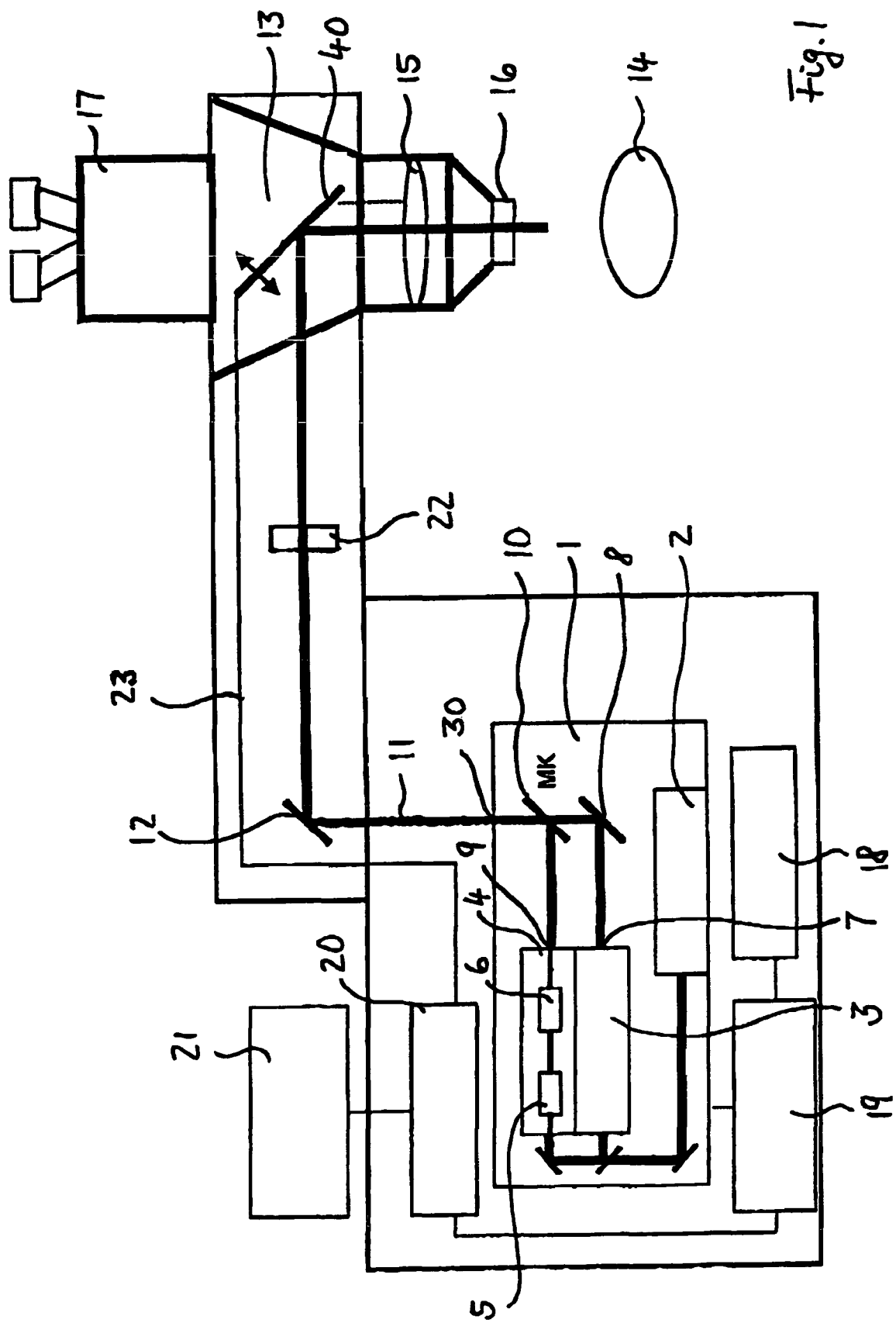

The invention involves a device and a procedure for refractive laser surgery on a target object.

Refractive laser surgery is used to correct eyesight defects of the human eye. Defective eyesight is one of humanity's main afflictions. In the developed industrial nations, ophthalmology has developed defective eyesight into a major field of medicine. Alongside the classic forms of eyesight correction, such as spectacles, contact lenses or the implantation of a new lens in the eye, recent years have seen the increasing use of eyesight correction by means of controlled tissue removal (ablation) from the surface of the cornea using laser. The laser most commonly used in is the excimer laser. Related techniques include PRK ("Photo Refractive Keratectomy"), LASIK (Laser-In-situ-Keratomileusis) and LASEK (Laser Epithelial Keratomileusis). These involve altering the surface shape and thus the focal distance of the cornea. The procedure used include both so-called "broad beam tissue removal" procedure and "scanning tissue removal" procedures: The scanning procedure involves the use of a scanner device to move the laser beam used in the treatment across the region of the eye that the treatment is to be performed on.

The LASIK procedure is currently the most commonly applied laser procedure in eyesight correction operations. LASIK is a combination of an operative "cutting technique" (Keramileusis) with PRK. In the LASIK procedure, the first step involves cutting a slice of the cornea (a "flap"), which is then tilted open rather in the manner of the cover of a book. It is then possible to remove the tissue from the cornea using an ultraviolet laser beam (UV laser beam) in order to correct the eyesight defect. At the end of the operation, the cornea slice is closed again. The cutting technique, together with the precision of the laser, permits a high level of accuracy in predicting the results of the treatment, even in cases involving large-scale corrections, as well as a swift recovery.

2. Description of Related Art

The application of laser beams with impulses of very short impulse duration in the range of femtoseconds (fs) was proposed for use in incisions into the cornea in the publication U.S. Pat. No. 5,984,916. Procedures have also been developed for so-called intrastromal refractive surgery using ultrashort impulses (*Der Ophthalmologe:* 98, 2001 623).

The use of fs-impulses to cut the cornea on the one hand, and the use of UV laser beams to remove tissue from the cornea on the other hand, render the application of this treatment method complicated for the user, since two very different laser systems have to be coordinated during the treatment process. The two laser systems have to be set up in such a way that the laser beam scanning the eye does not cause any unwanted damage to the eye. This entails a great deal of effort with respect to the technical apparatus.

The aim of the invention is the creation of an improved device and an improved procedure for refractive laser surgery, ones which are easier for the user in applying the treatment method for correcting eyesight defects and which raise the standard of safety while the operation is being performed.

The aim of the invention is fulfilled by the procedure as claimed herein.

BRIEF SUMMARY OF THE INVENTION

One important advantage of this invention over the current technology is that it becomes no longer necessary to separate scanner-devices for the application of fs-impulse laser beams and UV laser beams. This leads to saving materials and costs.

Moreover, the new refractive laser surgery device is constructed in a compact way so that less space is required to accommodate it in treatment rooms. During the cutting of the cornea and the subsequent removal of tissue from the cornea, the eye to be corrected needs only to be positioned with respect to a single scanner device. There is no need for the scanner device to be changed between the steps in the treatment involving the application of fs-impulse laser beams and UV laser beams, so that the position of the eye to be treated relative to the scanner device is maintained.

A further advantage of using one and the same scanner device for fs-impulse laser beams and UV laser beams during the eyesight defect correction operations, is that it is only necessary to monitor safety standards on the single scanner device. This leads to a reduction in the cost and effort involved in maintaining safety requirements.

An optimal further development of the invention involves at least a partial overlap of one optical path of the fs-impulse laser beam from the first optical output to the shared scanner device and a second optical path of the UV laser beam from the second optical output to the common scanner device, so that a partially shared optical path is formed. This removes the need to apply a separate safety measures, such as for instance, laser beam blocking switches, both for the fs-impulse laser beam and for the UV laser beam. It is sufficient for safety measures to be applied in the area of the shared optical path.

For the formation of the shared partial optical path, it is envisaged that an optimal realisation of the invention incorporates an optical component for the purpose of locking in the fs-impulse laser beam from the first optical output and/or the UV laser beam from the second optical output into the shared part of the path. This optical component could for instance take the form of a divided mirror, a dichrotic mirror, a prism or a diffractive optical element.

There is a way to meet and maintain safety requirements, especially with respect to the need to block the laser beam in case of moments of danger during the eyesight defect correction operation, that can be easily implemented in a preferred further development of the invention. This would involve the placement of safety mechanisms in the area of the shared optical path so that those safety means can be used to manipulate both the fs-impulse laser beam and the UV laser beam.

Technical complications arising during the construction of the device of refractive laser surgery can be reduced in an optimal further development of the invention by the inclusion of an optical guidance mechanism of the fs-impulse laser beam and the UV beam in the scanner device. The optical guidance mechanism could for instance take the form of a mirror whose surface is treated in such a way that it reflects the wavelength of the fs-impulse laser beam and the wavelength of the UV laser beam.

An optimal further development of the invention provides a common means of manipulating the radiation of the fs-impulse laser beam and the UV laser beam with the help of a shared optical component, for instance for the purpose of ensuring that safety standards are maintained, by the integration of the first laser beam source and the second laser beam source in one laser beam device with one optical output, whereby the fs-impulse laser beam and the UV laser beam are emitted through the optical output of the laser beam device.

In an optimal realisation of the invention, a compact and cost-effective device for refractive laser surgery is obtained by having a common pump source for the optical pumping of both laser beam sources.

A preferred way of realising the invention involves a cascaded sum frequency mixer for generating the UV laser beam, which enables a laser beam from the vicinity of the infrared zone to be transformed into a UV laser beam. This offers the benefit of avoiding the disadvantages, such as bad beam profile and poisonous materials, associated with the excimer laser.

A beneficial aspect of a further development of the invention is that the cascaded sum frequency mixer is a frequency quadrupler, for example of the type ($\omega+\omega\rightarrow 2\omega$; $2\omega+2\omega\rightarrow 4\omega$) or ($\omega+\omega\rightarrow 2\omega$; $\omega+2\omega\rightarrow 3\omega$; $3\omega+\omega\rightarrow 4\omega$). This enables the generation of wavelength frequencies $\geqq 205$ nm, though this lie above the 193 nm wavelength limit hitherto clinically licensed. A three-step frequency quadrupling also enables the generation of UV wavelength significantly lower than 200 nm.

It can be envisaged that the other laser beam source is an excimer laser.

To guarantee an optimal laser treatment when the target object—the eye—moves, an optimal realisation of the invention involves a tracking device to track the movements of the target object, whereby the tracking device is connected with the scanner device so that the scanning of the target object with the laser beam can be made dependent on the measurements of the tracking device.

In the preferred realisation of the invention, the first laser beam source is a fiber laser amplification system with impulse energies in the range of approximately a few µJ and subsequent impulse frequencies in a range of up to 1 MHz. The high subsequent impulse frequencies offer the benefit of shortening the processing time when the laser beam is applied.

The advantages of the device and its further developments described in the above paragraphs yield beneficial effects especially when the device is used to perform an application of the LASIK procedure on the eye ("LASIK"—Laser-In-situ-Keratomileusis), since both the incision of the cornea and the removal of corneal tissue can be performed using the same device.

Claims concerning the procedure that are dependent on corresponding claims concerning the device show those advantages mentioned in connection with the respective claim about the device.

DETAILED DESCRIPTION OF THE INVENTION

In the following, the invention will be explained with the help of an embodiment and by making reference to FIG. 1.

In accordance with FIG. 1, a device for refractive laser surgery comprises a laser device 1, a pump laser 2 for the optical pumping of a laser beam source 3 to produce an fs-impulse laser beam and another laser beam source 4 for UV laser beams. The preferred lasers used for the pump laser 2 are diode-pumped hard-bodied lasers which generate light with a wavelength in the vicinity of the infra-red region, for instance 1064 nm or 1054 nm. Subsequent frequency doubling yields a pump beam in the green spectral region.

The pump laser 2 is used to excite the first laser beam source 3 and the second laser beam source 4, both of which are formed, for instance, as a Ti:Sa-laser. A frequency conversion of the Ti:Sa-laser enables a region below 210 nm to be exploited, by doubling the converted Ti:Sa-laser at 840 nm, or by mixing a sequential sum frequency of 795 nm (amplification maximum) to a beam of less than 200 nm. At the same time, on account of its wide frequency range, the active laser material Ti:Saphir offers the possibility of generating and amplifying very short impulses, for example fs-impulses.

In the second light source 4, the light output of an original beam source 5 is subjected to frequency quadrupling using cascades sum frequency mixer 6, for the purpose of generating the UV laser beam. With the aid of the cascaded sum frequency mixer 6, it is possible to perform a frequency quadrupling: (1) $\omega+\omega\rightarrow 2\omega$; $2\omega+2\omega\rightarrow 4\omega$), or (2) $\omega+\omega\rightarrow 2\omega$; $\omega+2\omega\rightarrow 3\omega$; $3\omega+\omega\rightarrow 4\omega$. This permits the generation of a UV laser beam with wavelength in the region above and below 200 nm, starting from an original beam source 5, which delivers light in the region of the infrared zone.

Alternatively, an excimer-laser can be used as radiation source for the UV laser beams. Owing to its ready availability, this type of laser, e.g. ArF:excimer lasers, is currently virtually the only type use in ophthalmology for correcting eyesight defects. However, in comparison with Ti:Sa-laser, excimer lasers have a relatively bad beam quality and also require the use of a poisonous/caustic gas (fluorine) for their operation, this constituting a risk factor when the gas is produced and stored in treatment rooms.

The fs-impulse laser beam leaves the laser source 3 through an optical output 7 and is guided by an optical guidance component 8, for instance a mirror or a prism. The UV laser beam leaves the second laser source 4 through an optical output 9. By means of an optical component 10, the fs-impulse laser beam and the UV laser beam are locked into a shared optical path 11. The optical component 10 can take the form, for instance, of a divided mirror, a dichriotic mirror, a prism or a suitable diffractive optical element. The fs-impulse laser beam and the UV laser beam leave the laser device 1 through a laser device output 30. With the aid of an optical transmission device 12, the fs-impulse laser beam and the UV laser beam are transmitted to a scanner 13, which is used to train the laser beams onto a target object. For the purpose of guiding the laser beams, both the fs-impulse laser beam and the UV laser beam, onto the target object 14, guidance mechanisms 40 of the scanner 13 are designed in an appropriate way, for example, by means of a surface coating, so that laser beams with different wavelengths can be guided. Following the guidance of the beams, they pass through a focussing device 15 which serves to focus the laser beams onto the target object 14.

A Tracking device 16 is envisaged in order to be able to make allowance for movements of the target object 14 during the scanning of the target object 14 with the laser beam. This enables immediate reaction to movements of the target object 14 during scanning, thus allowing the laser beam to be positioned with a higher degree of precision on the surface of the target object 14.

With the aid of a monitoring system (17), the individual treatment steps of the refractive laser surgery can be observed on the target object (14).

Further items envisaged for the operation of the laser device 1, in accordance with FIG. 1, are a cooling device 18 especially to cool the pump laser 2, a power supply 19, and a control device 20. The control device 20 is connected to the operating unit 21 so that a user can control the laser device 1 with the aid of the operating unit 21. The control device 20 is furthermore connected by a cable 23 with the scanner device 13.

In the shared optical path 11, a safety component 22 is installed for regulating and blocking the passage of the fs-impulse laser beams and the UV laser beams. By opening and closing the safety component 22, the fs-impulse laser beams and the UV laser beams for the treatment fo the target object 14 are allowed to pass through to the scanner device 13 or are blocked. Thus, in order to be able to block all therapeutical laser beams falling on the target object in a moment of danger, it is only necessary to monitor the safety component 22. In order for it to fulfill the task described, the safety component 22 can be positioned at any point along the shared optical path 11, for example, directly on the laser device output 30, or before the scanner device 13.

Using the device described, it is possible to perform refractive laser surgery in such a way that an fs-impulse laser beam is used to cut a slice of the cornea ("flap"). This flap can then be tilted open to one side, so that a correction of the eyesight defect can be carried out using a UV laser beam. The use of Ti:Sa-lasers has the advantage that the active laser material Ti:Saphir makes possible very high subsequent frequencies for the amplified-laser beam ($\geq 1$ kHz). This in turn enables the reduction of the time needed for cutting the cornea and the consequent ablation of the cornea for refractive correction of the cornea when using UV laser beams, due to the high subsequent frequencies. Ti:Sa-lasers make possible impulse frequencies up to the range of a few hundred kHz. However, the time-saving advantage exists, independently of the laser medium, also for other laser beam sources with high subsequent frequencies.

The features of the invention as described above, shown in the FIGURE and described in the claims, can be of importance for the realisation of the invention in its various forms of embodiment, whether applied singly or in any combination.

The invention claimed is:

1. Procedure for refractive laser surgery on a target object (14), comprising the following steps:
   (a) producing a femtosecond-pulse (fs-pulse) laser beam using a first laser beam source (3),
   (b) producing a UV laser beam using a second laser beam source (4),
   (c) directing the fs-pulse laser beam and the UV laser beam across a shared scanner device (13) for scanning onto the target object,
   wherein the fs-pulse laser beam travels along one optical path from one optical output (7) to the shared scanner device (13), the UV laser beam travels along a second optical path from a second optical output (9) to the shared scanner device (13), and in doing so, the fs-pulse laser beam and the UV laser beam travel at least partially along a shared part of the first and second optical paths (11) due to an overlap between the first optical path and the second optical path;
      and wherein the fs-pulse laser beam and the UV laser beam are guided with the aid of an optical guidance mechanism of the scanner device (13) and,
      cutting a slice of the cornea of the eye by using the fs-laser bean and performing an eyesight correction operation by using the UV laser beam.

2. Procedure as per claim 1, further comprising locking the fs-pulse laser beam emitted from the first optical output (7) and/or the UV laser beam emitted from the second optical output (9) into a shared part of the first and second optical paths (11) with the aid of an optical component (10).

3. Procedure as per claim 1, wherein the first laser beam source (3) and the second laser beam source (4) are integrated into a laser beam device (1) with a single optical output, such that the fs-pulse laser beam and the UV laser beam are emitted from the single optical output of the laser beam device (1).

4. Procedure as per claim 1, wherein the first laser beam source (3) and the second laser beam source (4) are optically pumped with a shared pumped light source (18).

5. Procedure as per claim 1, comprising scanning of the target object (14) with the aid of a tracking device (16) connected to the shared-scanner device (13) for the purpose of tracking a movement of the target object (14).

* * * * *